United States Patent
Leflaive et al.

(10) Patent No.: US 7,759,534 B2
(45) Date of Patent: *Jul. 20, 2010

(54) PROCESS AND DEVICE FOR IMPROVED SEPARATION OF PARAXYLENE IN A SIMULATED MOVING BED

(75) Inventors: Philibert Leflaive, Mions (FR); Lue Wolff, Chaponnay (FR); Damien Leinekugel Le Cocq, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 109 days.

This patent is subject to a terminal disclaimer.

(21) Appl. No.: 12/181,771

(22) Filed: Jul. 29, 2008

(65) Prior Publication Data
US 2009/0018380 A1    Jan. 15, 2009

(30) Foreign Application Priority Data
Jul. 30, 2007   (FR) .................................. 07 05615

(51) Int. Cl.
*C07C 7/12* (2006.01)
(52) U.S. Cl. ...................... 585/828; 585/820; 585/826; 585/825; 585/827
(58) Field of Classification Search ................. 585/820, 585/828
See application file for complete search history.

(56) References Cited

U.S. PATENT DOCUMENTS

| | | | |
|---|---|---|---|
| 5,902,486 A | 5/1999 | Couenne et al. | |
| 6,376,734 B1 | 4/2002 | Magne-Drisch et al. | |
| 6,838,588 B2 * | 1/2005 | Leflaive et al. | 585/828 |
| 6,841,714 B2 * | 1/2005 | Leflaive et al. | 585/828 |
| 7,390,412 B2 * | 6/2008 | Pavone | 210/659 |
| 7,473,368 B2 * | 1/2009 | Hotier | 210/659 |
| 2002/0143223 A1 * | 10/2002 | Leflaive et al. | 585/820 |
| 2003/0069461 A1 | 4/2003 | Leflaive et al. | |
| 2004/0256323 A1 * | 12/2004 | Pavone | 210/659 |

FOREIGN PATENT DOCUMENTS

| | | |
|---|---|---|
| EP | 0 875 268 A1 | 11/1998 |
| FR | 2 795 407 A1 | 12/2000 |
| FR | 2 829 758 A1 | 3/2003 |
| FR | 2 856 313 A1 | 12/2004 |

* cited by examiner

*Primary Examiner*—Tam M Nguyen
(74) *Attorney, Agent, or Firm*—Millen, White, Zelano & Branigan, P.C.

(57) ABSTRACT

Process for separating paraxylene with a purity that is at least equal to 99.5% by weight from an aromatic feedstock F in a single adsorption stage in a simulated moving bed (SMB), comprising different numbers of beds, allocated to a zone 1 between the supply of the desorbent D and the draw-off of the extract E; a zone 2 between the draw-off of the extract E and the supply of the feedstock F; a zone 3 between the supply of the feedstock and the draw-off of the raffinate R; a zone 4 between the draw-off of the raffinate R and the supply of the desorbent D, wherein an SMB of 12 adsorbent beds has bed configuration (2, 5, 3, 2), an SMB of 15 adsorbent beds has bed configuration (3, 6, 4 , 2), or an SMB of 19 adsorbent beds has bed configuration (4, 7, 6, 2), wherein the desorbent in this latter case is paradiethylbenzene.

8 Claims, 2 Drawing Sheets

[Key to Fig. 1:]

Rendement = Yield

Nombre de lits = Number of Beds

[Key to Fig. 2:]

Rendement = Yield

Nombre de lits = Number of Beds

PROCESS AND DEVICE FOR IMPROVED SEPARATION OF PARAXYLENE IN A SIMULATED MOVING BED

CROSS-REFERENCE TO RELATED APPLICATION

This application is related to Ser. No. 12/181525, entitled "Process And Device For Improved Separation Of Metaxylene In A Simulated Moving Bed", by inventors Philibert Leflaive, Damien Leinekugel-Le-CocQ and Luc Wolff, filed Jul. 29, 2008, claiming priority of French application serial no. 07/05.616, filed Jun. 30, 2007, the cross reference application being incorporated by reference herein.

FIELD OF THE INVENTION

The invention relates to the field of the separation of paraxylene (PX) from an aromatic hydrocarbon feedstock with essentially 8 carbon atoms. "Essentially" is defined as the fact that the feedstock contains at least 95% xylenes, and preferably at least 97% xylenes, whereby the other components can be of any type.

This type of feedstock can be separated by distillation with difficulty. A family of adsorption processes and associated devices is then used, known under the name of processes or devices for "chromatographic" separation or "in a simulated moving bed," or "in simulated countercurrent," or "in simulated co-current," that we will designate below by the name of "SMB" processes and devices (for "Simulated Moving Bed" according to the English terminology, which "Lit Mobile Simulé" means).

The SMB separation of the paraxylene of commercial purity, typically with at least 99.7% by weight, is carried out industrially in the SMB devices that comprise 24 adsorbent beds. A raffinate that is high in ethylbenzene (EB), orthoxylene (OX) and metaxylene (MX), often recycled in the SMB after isomerization, is also produced.

The invention relates to an SMB separation process that makes it possible to obtain—in a single stage—PX with a commercial purity of more than 99.5% and typically 99.7% by weight, in less complex SMB devices than those of the prior art, in particular with a small number of adsorbent beds and specific configurations of the adsorption/desorption zones.

PRIOR ART

The SMB chromatographic separation is well known in the prior art. As a general rule, a simulated moving bed comprises at least three chromatographic zones, and optionally four or five, whereby each of these zones consists of at least one bed or a portion of column and is located between two successive supply or draw-off points. Typically, at least one feedstock F to be fractionated and one desorbent D (sometimes called eluant) are supplied, and at least one raffinate R and one extract E are drawn off. The supply and draw-off points are changed over time, typically offset toward the bottom of one bed in a synchronous manner.

By definition, each of the operating zones is designated by a number:
Zone 1=Desorption zone of the desired product (here, paraxylene that is contained in the extract) located between the injection of the desorbent D and the sampling of the extract E;
Zone 2=Desorption zone of the compounds of the raffinate, located between the sampling of the extract E and the injection of the feedstock that is to be fractionated F;
Zone 3=Adsorption zone of the desired product (paraxylene), located between the injection of the feedstock and the draw-off of the raffinate R, and;
Zone 4, located between the draw-off of the raffinate and the injection of the desorbent.

The separation process in an SMB device therefore operates according to a configuration (a, b, c, d) with:
a=Number of adsorbent beds operating in zone 1;
b=Number of adsorbent beds operating in zone 2;
c=Number of adsorbent beds operating in zone 3;
d=Number of adsorbent beds operating in zone 4.

According to a variant of a separation unit in a simulated moving bed SMB, it is also possible to produce two distilled raffinates R1 and R2 of different compositions. R1 is the "first raffinate," or "intermediate raffinate," and R2 is the second raffinate.

In this case, the SMB separation unit then comprises an increased number of operating zones that are delimited by the injections of the feedstock, the desorbent, and the draw-offs of an extract that contain the desired product, an intermediate raffinate (or first raffinate), and a second raffinate. The two raffinates have different compositions. For example, for a separation of a C8-aromatic fraction, in which the extract is the desired product, the first raffinate (or intermediate raffinate) is typically relatively high in ethylbenzene and relatively low in orthoxylene and metaxylene, whereas the second raffinate is, in contrast, relatively low in ethylbenzene and relatively high in orthoxylene and metaxylene.

According to this variant, the zones 1, 2 and 4 are not modified. In contrast, the zone 3 is divided between a zone $3_A$ and a zone $3_B$, or:
Zone $3_A$ for adsorption of the desired product, located between the injection of the feedstock and the draw-off of the intermediate raffinate;
Zone $3_B$ for adsorption of the main product of the intermediate raffinate, located between the draw-off of the intermediate raffinate and the draw-off of the second raffinate.

According to the invention, the zones $3_A$ and the zone $3_B$ are regarded as forming part of the same zone 3.

In an in-depth way, the prior art describes various devices and processes that make it possible to carry out the separation of feedstocks in a simulated moving bed. It is possible to cite in particular the U.S. Pat. Nos. 2,985,589, 3,214,247, 3,268, 605, 3,592,612, 4,614,204, 4,378,292, 5,200,075, and 5,316, 821. These patents also describe in detail the operation of an SMB.

The SMB devices typically comprise at least one column (and often two), adsorbent beds Ai that are placed in this column, separated by plates Pi with chamber(s) Ci for distributing and/or extracting fluids in or from various adsorbent beds, and controlled sequential means for distributing and extracting fluids.

These controlled means for distributing and extracting fluids from an SMB are typically one of the following two major types of technology:
Either, for each plate, a number of all-or-nothing controlled valves for the supply or the draw-off of fluids, whereby these valves are typically located in the immediate vicinity of the corresponding plate and that comprise in particular, for each plate Pi, at least 4 all-or-nothing controlled two-way valves for respectively the supply of fluids F and D and the draw-off of fluids E and R.
Or a multiple-path rotary valve for the supply or the draw-off of fluids on the set of plates.

The separation of the paraxylene from aromatic fractions is typically carried out in two ways:

In a first path, a so-called "hybrid path," an SMB separation is carried out that makes it possible to obtain low-purity PX, for example 95%, which is then purified by crystallization to obtain high-purity PX, typically a commercial purity of 99.7% or more.

In a second path, a so-called "stand-alone" (direct) path, an SMB separation is carried out that makes it possible to obtain high-purity PX directly, typically of 99.7% or more. This process also makes it possible to obtain a raffinate that is high in ethylbenzene, orthoxylene and metaxylene, often recycled in the SMB after isomerization. All the commercial SMB units of this type operate with 24 adsorbent beds, because it is considered that this number of adsorbent beds is necessary to obtain the PX at the high purity that is desired, more than 99.5% and typically at least 99.7% by weight, or at least to obtain this purity with an acceptable yield of PX. The higher the number of beds, the closer it is possible to come to an actual fluid/adsorbent counter-current, which is a continuous process, equivalent to a process with an infinite number of beds. Thus, for the high-purity PX, it is assumed that 24 beds are necessary to obtain the desired purity and an acceptable yield.

Such an SMB separation unit is operated in general at a temperature of between 20° C. and 250° C., preferably between 90° C. and 210° C., and more preferably between 160° C. and 200° C., and under a pressure of between the bubble pressure of the xylenes at the operating temperature and 2 MPa. The desorbent that is used in the SMB unit is generally selected from among paradiethylbenzene (or PDEB), toluene, paradifluorobenzene or diethylbenzenes in a mixture. The volumetric ratio of the desorbent to the feedstock in the SMB unit is typically between 0.5 and 2.5, and preferably between 1.05 and 1.7. It will also be possible to refer to the above-mentioned patent applications or patents or the following: U.S. Pat. No. 2,985,589; FR 2681066; U.S. Pat. No. 6,063,978; WO 05/054,161, or to articles by Anjushri S. Kurup et al., Ind. Eng. Chem. Res. 2005, 44, 5703-5714 or by Pedro Sa Gomes et al., Adsorption (2006) 12:375-392. These last two articles clearly indicate that the separation of the high-purity PX is done in 24 adsorbent beds.

SIMPLIFIED DESCRIPTION OF THE INVENTION

The invention relates to an SMB separation process that makes it possible to obtain, in a single stage, PX with a purity of higher than 99.5% and typically with the commercial purity of 99.7% by weight, in SMB devices that are less complex than those of the prior art, in particular with a reduced number of adsorbent beds. It has actually been discovered that contrary to what was considered previously, obtaining a high purity by SMB in a direct path was possible with a limited number of adsorbent beds, provided that a double selection was simultaneously carried out:

Specific number of adsorbent beds,
Specific configuration of zones (a, b, c, d).

More specifically, it was found that it was possible to obtain unexpected performance levels that are industrially advantageous by using in combination:

12 beds in configuration (2, 5, 3, 2), or else:
15 beds in configuration (3, 6, 4, 2), or else:
19 beds in configuration (4, 7, 6, 2).

This last double selection is actually primarily high-performing when the PDEB (paradiethylbenzene) is used as a desorbent.

DETAILED DESCRIPTION OF THE INVENTION

The invention therefore proposes a process for separating paraxylene with a purity of at least 99.5% by weight, and preferably at least 99.7% by weight, from a feedstock F of aromatic hydrocarbons having essentially 8 carbon atoms, by direct separation into a single stage of adsorption in a simulated moving bed in an SMB device with at least one column that comprises a number of adsorbent beds that are separated by distribution/extraction plates $P_i$, in which at least the feedstock F and one desorbent D are fed into this device, and at least one extract E that is high in paraxylene and at least one raffinate R are drawn off, whereby the supply and draw-off points are changed over time with a switching time T and determine a number of operating zones of the SMB, and in particular the following primary zones:

A zone 1 for desorption of paraxylene that is located between the supply of the desorbent D and the draw-off of the extract E;

A zone 2 for desorption of the compounds of the raffinate, located between the draw-off of the extract E and the supply of the feedstock F;

A zone 3 for the adsorption of at least the paraxylene, located between the supply of the feedstock and the draw-off of the raffinate R;

A zone 4 that is located between the draw-off of the raffinate R and the supply of the desorbent D, whereby the process is carried out according to a configuration of zones (a, b, c, d) with:

a=Number of adsorbent beds operating in zone 1;
b=Number of adsorbent beds operating in zone 2;
c=Number of adsorbent beds operating in zone 3;
d=Number of adsorbent beds operating in zone 4, whereby the process implements one of the following options:

Either an SMB of 12 adsorbent beds operating according to the configuration (2, 5, 3, 2) is used, Or an SMB of 15 adsorbent beds operating according to the configuration (3, 6, 4, 2) is used, Or an SMB of 19 adsorbent beds operating according to the configuration (4, 7, 6, 2) is used, whereby the desorbent in this latter case is paradiethylbenzene.

The use of these double selections makes it possible to obtain results that are superior to those of all of the other possible combinations for an identical or close number of adsorbent beds. The prior art had considered that obtaining paraxylene with a very high purity required a process that was close to a simulated real countercurrent (continuous process that is equivalent to a process with an infinite number of beds), and therefore a high number of beds: typically 24.

It is thought, according to the invention, that certain configurations with a reduced number of beds have a distribution of zones that lends itself particularly well to separation, and that the latter leads to unsuspected performance levels, with an SMB with a reduced number of beds, which is particularly economical (fewer controlled valves, fewer distribution/extraction systems, fewer pipes).

Preferably, the SMB option of 12 adsorbent beds operating according to the configuration (2, 5, 3, 2) and the SMB option of 15 adsorbent beds operating according to the configuration (3, 6, 4, 2) are implemented with a desorbent that belongs to the group that is formed by toluene and paradiethylbenzene.

The SMB option of 19 adsorbent beds operating according to the configuration (4, 7, 6, 2) is implemented with paradiethylbenzene (PDEB) as a desorbent.

Preferably, for a given SMB, the operation is performed with conditions (in particular flow of feedstock and flow of solvent) that make it possible to obtain a purity of 99.7% by weight, i.e., the typically desired commercial purity.

Figure 1:
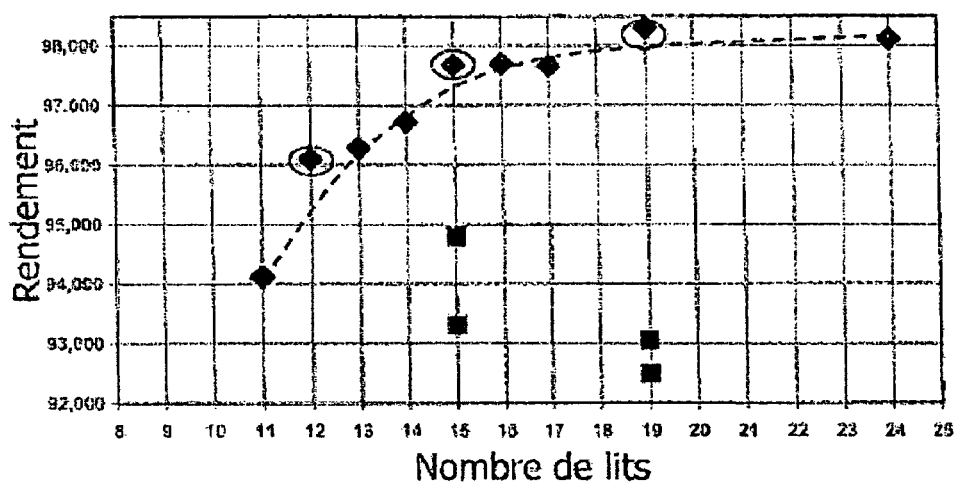
FIG. 1 shows the yield of paraxylene of the SMB based on the number of adsorbent beds for various zone configurations in an SMB operating with toluene as a desorbent.

The interpretation of these figures will be discussed in the following examples.

EXAMPLES

The invention will be better understood from reading the following examples, in which:

Example 1 is representative of the prior art in a "stand alone" version (direct separation in one stage) for a purity≧99.5 in which an SMB device with 24 adsorbent beds is used, with toluene as a desorbent.

Example 2 describes the performance levels of an SMB device that has the same overall adsorbent volume as that of Example 1, but distributed between a smaller number of beds, according to various zone configurations and also using toluene as a desorbent. Certain bed number/zone configuration combinations are in accordance with the invention.

Example 3 is representative of the prior art in a "stand alone" version (direct separation in one stage) for a purity≧99.5, in which an SMB device with 24 adsorbent beds is used, with PDEB as a desorbent.

Example 4 describes the performance levels of an SMB device that has the same overall volume of adsorbent as that of Example 3, but distributed between a smaller number of beds, according to various zone configurations and also using PDEB as a desorbent. Certain bed number/configuration combinations are in accordance with the invention.

Comparative Example 1

According to the Prior Art

Paraxylene is separated from an aromatic feedstock with 8 carbon atoms on an SMB device in a simulated moving bed that is equipped with 24 adsorbent beds and that uses toluene as a desorbent.

This SMB device comprises 24 adsorbent beds with a 1.1 m height and a $3.5 \times 10^{-4}$ m$^2$ internal section, with an injection of feedstock, an injection of desorbent, a draw-off of extract, and a draw-off of raffinate. The typical effective zone configuration is (5, 9, 7, 3), or:

5 beds in zone 1;
9 beds in zone 2;
7 beds in zone 3;
3 beds in zone 4.

The adsorbent that is used is a BaX-type zeolite, and the desorbent is toluene. The temperature is 175° C., and the pressure is 1.5 MPa.

The feedstock F consists of 20% PX, 22% OX, 48% MX, and 5% EB. The switching time that is used is 71 seconds. The liquid flow rates in the various zones are as follows:

4.78 cm$^3 \cdot$s$^{-1}$ in zone 1;
3.96 cm$^3 \cdot$s$^{-1}$ in zone 2;
4.99 cm$^3 \cdot$s$^{-1}$ in zone 3;
3.24 cm$^3 \cdot$s$^{-1}$ in zone 4.

A PX purity in the extract of 99.85% by weight and a PX yield (ratio of the PX of the extract to the PX of the feedstock) of 95.75% by weight are then obtained, by simulation.

Example 2

The PX is separated from the same feedstock F in an SMB device that comprises an adsorber that has the same diameter and the same overall volume of the same adsorbent as the one of Example 1, but distributed between a number n of beds that is less than 24, according to various zone configurations. For this purpose, adsorbent beds with a height $L_n=24/n \times L_{24}$ are considered, with:

$L_n$=bed height in the SMB with n beds.
$L_{24}$=bed height in the SMB with 24 beds.

This SMB also uses toluene as a desorbent.

All the tests are carried out with an isopurity of 99.85% by weight, which is the purity that is obtained in Example 1, isoflow of desorbent D and feedstock F relative to Example 1.

In addition, so as to preserve the ratio between the liquid flow rates and the equivalent solid flow rate in each zone, the switching time $T_n$ of the same factor as the height of the beds is adapted relative to the switching time $T_{24}$ of the SMB with 24 beds: $T_n=24/n \times T_{24}$. This value is then slightly corrected so as to make it isopure and therefore to allow a comparison of the different systems based on the yields.

The yield obtained in PX for different numbers of beds, located between 9 and 19, and with various zone configurations, was tested by simulation.

FIG. 1 shows (in diamond-shaped dots) the curve of the yield that is obtained for each number of beds and for the best possible zone configuration. A mean curve was plotted in dotted lines, and the noteworthy yield dots were circled. Certain additional dots (square-shaped dots), corresponding to other non-optimum configurations, were also shown.

Surprisingly enough, it is seen that the curve of evolution of the yield with the number of beds exhibits 2 optimum configurations: the SMB with 12 and 15 beds, which become detached from the mean curve for their optimum configuration. The dot corresponding to 11 beds is also above the curve, but the yield that is obtained is still only moderate. It is also seen that for the two SMB with 12 and 15 beds, the other configurations lead to considerably lower yields. This is reflected in Tables 1 and 2 below. Only the best configurations that make it possible to obtain the desired degree of purity are mentioned.

TABLE 1

Study of the Influence of the Zone Configuration in the 15-Bed Case.

| Configuration | Yield of Paraxylene |
| --- | --- |
| 3, 6, 4, 2 | 95.26% |
| 4, 5, 4, 2 | 89.58% |
| 3, 5, 5, 2 | 88.76% |

TABLE 2

Study of the Influence of the Zone
Configuration in the 12-Bed Case.

| Configuration | Yield of Paraxylene |
|---|---|
| 2, 5, 3, 2 | 93.26% |
| 2, 4, 4, 2 | 85.20% |
| 2, 4, 2, 4 | 81.83% |

The physical interpretation of these results is not obvious. One possible explanation is that the association of a particular number of beds with a particular zone configuration can prove quite superior to other possibilities for the effectiveness of separation and yield. The importance of this double selection: number of beds/zone configurations had not been taken into consideration in the prior art of the separation of the PX, which, moreover, considers that obtaining high-purity PX requires 24 beds.

Comparative Example 3

According to the Prior Art

The PX is separated from the same feedstock F in an SMB device that is identical to that of Example 1, with a zone configuration that is also identical.

Unlike Example 1, the desorbent that is used is paradiethylbenzene (PDEB).

The operating conditions and the liquid flow rates in the various zones are identical to those of Example 1. The switching time that is used is slightly different and is 70.4 seconds.

By simulation, the same purity of PX in the extract of 99.85% by weight and a yield of PX (ratio of the PX of the extract to the PX of the feedstock) of 98.12% by weight are then obtained.

Example 4

The same tests as those of Example 2, but with paradiethylbenzene (PDEB) as a desorbent, are carried out. The number of adsorbent beds and the configuration of zones are therefore made to vary, but with PDEB and not toluene as a desorbent.

All of the tests are carried out with an isopurity of 99.85% by weight, which is the purity that is obtained in Example 3, isoflow of desorbent D and feedstock F relative to Example 3, to compare the results that are obtained with that of the prior art (Example 3) with the desorbent PDEB.

Figure 2:
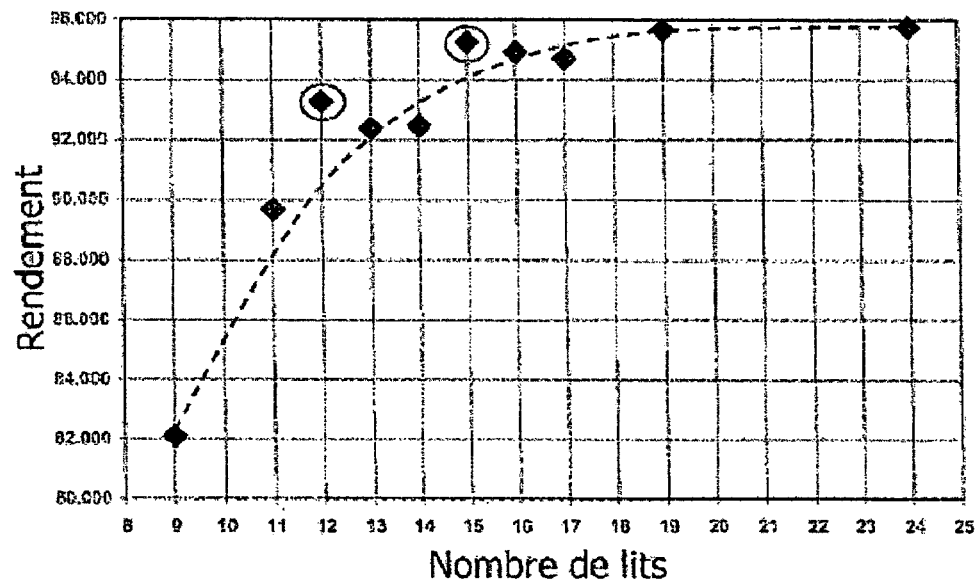
FIG. 2 shows the yield of paraxylene of the SMB based on the number of adsorbent beds for various zone configurations in an SMB operating with the PDEB as a desorbent.

FIG. 2 shows (in diamond-shaped dots) the same curve of the yield—that is obtained for each number of beds and for the best possible zone configuration—as that of Example 2, but with PDEB as a desorbent.

Analogously, a mean curve was plotted in dotted lines, and the noteworthy yield dots were circled. Certain additional dots (square-shaped dots), corresponding to other non-optimum configurations, were also shown.

Surprisingly enough, it is seen that the curve of evolution of the yield with the number of beds exhibits 3 optimum configurations this time: the SMB with 12 and 15 beds, which become detached—as for FIG. 1—from the mean curve for their optimum configuration, which is the same as that of Example 2 with the desorbent toluene. In addition, however, the 19-bed dot also provides very good results that are even superior to those that are obtained with 24 beds (prior art). This is reflected in Tables 3, 4 and 5 below. Only the best configurations that make it possible to obtain the desired degree of purity are mentioned.

TABLE 3

Study of the Influence of the Zone
Configuration in the 15-Bed Case

| Configuration | Yield of Paraxylene |
|---|---|
| 3, 6, 4, 2 | 97.68% |
| 4, 5, 4, 2 | 93.32% |
| 3, 5, 5, 2 | 94.80% |

TABLE 4

Study of the Influence of the Zone
Configuration in the 12-Bed Case

| Configuration | Yield of Paraxylene |
|---|---|
| 2, 5, 3, 2 | 96.10% |
| 2, 4, 4, 2 | 91.64% |
| 2, 4, 2, 4 | 80.74% |

TABLE 5

Study of the Influence of the Zone
Configuration in the 19-Bed Case

| Configuration | Yield of Paraxylene |
|---|---|
| 4, 7, 6, 2 | 98.01% |
| 5, 6, 6, 2 | 93.05% |
| 4, 6, 6, 3 | 92.50% |

The physical interpretation of these new results is no longer obvious. One possible explanation is that the desorbent PDEB, also associated with a particular number of beds: 19, with a particular zone configuration, also improves the effectiveness of separation and the yield in the 19-bed case.

The result of the preceding examples is that the following combinations are the most high-performing, according to the invention:

SMB of 12 adsorbent beds operating according to the configuration (2, 5, 3, 2),

SMB of 15 adsorbent beds operating according to the configuration (3, 6, 4, 2),

SMB of 19 adsorbent beds operating according to the configuration (4, 7, 6, 2), whereby the desorbent in this latter case is paradiethylbenzene.

The importance of this double selection: number of beds/zone configurations, and optionally its association with a particular solvent had not been taken into consideration in the prior art of the separation of the PX, which, moreover, considers that obtaining high-purity PX of at least 99.5% by weight requires 24 beds. Thus, to minimize the number of beds for a given desired separation, to optimum allocation of beds for each zone is determined for a series of SMB columns, each column having a different number of beds. In general, the adsorbent beds are both physically and chemically the same, but solvent selection may also contribute to the effectiveness of the separation.

The preceding examples can be repeated with similar success by substituting the generically or specifically described reactants and/or operating conditions of this invention for those used in the preceding examples.

In the foregoing and in the examples, all parts and percentages are by weight, unless otherwise indicated.

The entire disclosures of all applications, patents and publications, cited herein and of corresponding French application No. 07/05.615, filed Jul. 30, 2007, are incorporated by reference herein.

The invention claimed is:

1. A process comprising separating paraxylene (PX) with a purity of at least 99.5% by weight from a feedstock F of aromatic hydrocarbons having essentially 8 carbon atoms by direct separation into a single stage of adsorption in a simulated moving bed in at least one column comprising a number of adsorbent beds separated by distribution/extraction plates $P_i$, in which at least one feedstock F and one desorbent D are fed into the at least one column, and at least one extract E high in paraxylene and at least one raffinate R are drawn off, whereby the supply and draw-off points are changed over time with a switching time T providing a number of operating zones of the SMB column, including the following primary zones:

zone 1 for desorption of the paraxylene located between the supply of the desorbent D and the draw-off of the extract E;

zone 2 for desorption of the compounds of the raffinate, located between the draw-off of the extract E and the supply of the feedstock F;

zone 3 for the adsorption of at least paraxylene, located between the supply of the feedstock and the draw-off of the raffinate R;

zone 4 located between the draw-off of the raffinate R and the supply of the desorbent D, wherein the process is carried out conducted according to a configuration of zones (a, b, c, d) with:

a=Number of adsorbent beds operating in zone 1;
b=Number of adsorbent beds operating in zone 2;
c=Number of adsorbent beds operating in zone 3;
d=Number of adsorbent beds operating in zone 4;

said process being conducted according to one of the following options:

an SMB of 12 adsorbent beds operating according to configuration (2, 5, 3, 2),
an SMB of 15 adsorbent beds operating according to configuration (3, 6, 4, 2),
an SMB of 19 adsorbent beds operating according to configuration (4, 7, 6, 2), and, wherein the desorbent is paradiethylbenzene.

2. A process according to claim 1, in which the process is conducted by separating the PX in Either an SMB of 12 adsorbent beds operating according to configuration (2, 5, 3, 2 ),
an SMB of 15 adsorbent beds operating according to configuration (3, 6, 4, 2),
and in which the desorbent in both alternatives is toluene or paradiethylbenzene.

3. A process according to claim 1, comprising conducting the process in an SMB of 12 adsorbent beds operating according to configuration (2, 5, 3, 2).

4. A process according to claim 1, comprising conducting the process in an SMB of 15 adsorbent beds operating according to configuration (3, 6, 4, 2).

5. A process according to claim 1, comprising conducting the process in an SMB of 19 adsorbent beds operating according to configuration (4, 7, 6, 2) and wherein the desorbent is paradiethylbenzene.

6. A process according to claim 1, conducted with a sufficient feedstock flow rate and solvent flow rate to yield a PX purity of 99.7% by weight.

7. A process according to claim 2, comprising conducting the process in an SMB of 12 adsorbent beds operating according to configuration (2, 5, 3, 2).

8. A process according to claim 2, comprising conducting the process in an SMB of 15 adsorbent beds operating according to configuration (3, 6, 4, 2).

* * * * *

UNITED STATES PATENT AND TRADEMARK OFFICE
CERTIFICATE OF CORRECTION

PATENT NO. : 7,759,534 B2
APPLICATION NO. : 12/181771
DATED : July 20, 2010
INVENTOR(S) : Leflaive et al.

It is certified that error appears in the above-identified patent and that said Letters Patent is hereby corrected as shown below:

Column 9, line 10 reads: "lated moving bed in at least on column comprising a number"

Should read: --lated moving bed SMB in at least on column comprising a number--

Column 9, line 30 reads: "wherein the process is carried out conducted according to a"

Should read: --wherein the process is conducted according to a--

Signed and Sealed this

Twelfth Day of October, 2010

David J. Kappos
*Director of the United States Patent and Trademark Office*